United States Patent
Steinberg et al.

(10) Patent No.: US 12,146,729 B2
(45) Date of Patent: Nov. 19, 2024

(54) SYSTEMS AND METHODS FOR DETECTING AND IDENTIFYING EXPLOSIVES

(71) Applicant: Demining Development LLC, New York, NY (US)

(72) Inventors: Gabriel Steinberg, New York, NY (US); Jasper Baur, New York, NY (US)

(73) Assignee: SAFE PRO AI LLC, New York, NY (US)

( * ) Notice: Subject to any disclaimer, the term of this patent is extended or adjusted under 35 U.S.C. 154(b) by 0 days.

(21) Appl. No.: 18/232,325

(22) Filed: Aug. 9, 2023

(65) Prior Publication Data

US 2024/0219153 A1    Jul. 4, 2024

Related U.S. Application Data

(60) Provisional application No. 63/406,234, filed on Sep. 13, 2022.

(51) Int. Cl.
| | | |
|---|---|---|
| *F41H 11/13* | (2011.01) | |
| *G06V 10/80* | (2022.01) | |
| *G06V 10/82* | (2022.01) | |
| *G06V 20/17* | (2022.01) | |

(52) U.S. Cl.
CPC ............. *F41H 11/13* (2013.01); *G06V 10/80* (2022.01); *G06V 10/82* (2022.01); *G06V 20/17* (2022.01); *G06V 2201/05* (2022.01)

(58) Field of Classification Search
CPC .......... F41H 11/12; F41H 11/13; B63G 7/02; G06V 2201/05; G06V 20/17
See application file for complete search history.

(56) References Cited

U.S. PATENT DOCUMENTS

| | | | |
|---|---|---|---|
| 7,637,196 B2* | 12/2009 | Thornton | F41H 11/12 89/1.13 |
| 9,092,866 B1* | 7/2015 | Li | F41H 11/136 |
| 9,110,168 B2* | 8/2015 | Mohamadi | G01S 13/0209 |
| 9,329,001 B2* | 5/2016 | Mohamadi | F41H 11/16 |
| 9,361,539 B2* | 6/2016 | Li | G06V 10/457 |
| 10,948,587 B1* | 3/2021 | Boronse | G01S 13/887 |
| 11,140,326 B2* | 10/2021 | Lunt | G08G 5/0078 |
| 11,195,012 B1* | 12/2021 | Schroeder | G06V 10/82 |
| 11,299,270 B2* | 4/2022 | Culver | H04W 4/90 |
| 11,551,032 B1* | 1/2023 | Gebhardt | G01S 5/0018 |
| 11,823,364 B1* | 11/2023 | Shu | G06V 20/176 |
| 2002/0062730 A1* | 5/2002 | Thornton | F41H 11/12 86/50 |
| 2014/0062754 A1* | 3/2014 | Mohamadi | F41H 11/16 89/1.13 |
| 2020/0098130 A1* | 3/2020 | Porter | G06T 7/70 |
| 2020/0272837 A1* | 8/2020 | Brooks | G06V 10/56 |
| 2022/0074713 A1* | 3/2022 | Malka | G06F 16/29 |
| 2023/0124398 A1* | 4/2023 | Ampatzidis | G06V 20/188 382/110 |

(Continued)

*Primary Examiner* — Joshua E Freeman

(74) *Attorney, Agent, or Firm* — JWIP & Patent Services, LLC; Jacob G. Weintraub, Esq.

(57) ABSTRACT

The present invention is directed to systems and methods for aerially detecting and identifying explosives on the ground, and more specifically systems and methods for detecting and identifying landmines and unexploded ordnance (UXO) on the surface.

21 Claims, 7 Drawing Sheets

(56) References Cited

U.S. PATENT DOCUMENTS

| | | | |
|---|---|---|---|
| 2023/0292647 A1* | 9/2023 | Bainbridge | G06V 20/188 |
| | | | 702/2 |
| 2023/0314107 A1* | 10/2023 | Acker | G06F 18/23 |
| | | | 382/103 |
| 2023/0316555 A1* | 10/2023 | Spangenberg | G06V 10/82 |
| | | | 345/419 |
| 2023/0326012 A1* | 10/2023 | Takla | G06T 7/246 |
| 2024/0028636 A1* | 1/2024 | Jackson | G06V 20/17 |
| 2024/0193938 A1* | 6/2024 | Harikumar | G06V 20/194 |

* cited by examiner

SYSTEMS AND METHODS FOR DETECTING AND IDENTIFYING EXPLOSIVES

RELATED APPLICATIONS

This application claims priority to U.S. Provisional Patent Application No. 63/406,234, filed on Sep. 13, 2022; the entirety of which is incorporated herein by reference.

BACKGROUND OF THE INVENTION

Landmines and unexploded ordnance (UXO) pose an enormous threat to and significantly decrease the quality of life of hundreds of thousands of civilians throughout the world. Land release is the process of detecting all the landmines and UXO in a particular region, safely clearing these objects, and returning the land to the local population, devoid of any explosive hazards. The most dangerous and time-consuming part of the land release and mine clearance process is detection of the objects.

Despite efforts of demining organizations and the International Mine Ban Treaty, the number of LUXO is expected to continue to grow due to ongoing conflicts. In some examples, electromagnetic induction (EMI) and metal detection beep-and-prod methods are utilized by demining NGOs and state demining operations for landmine detection. EMI can be effective for the detection of large metallic debris but requires extremely laborious and precise work often in very harsh environmental conditions. EMI and metal detection beep-and-prod methods can include several disadvantages such as high false alarm rate, the inability to detect small, low-metal landmines and/or the inability to detect and clear seismically activated mines.

An example mine that exploits the flaws of EMI is the Russian-made POM-3. This mine uses a seismic sensor to detonate if a person is within about 16 meters of it, prohibiting standard detection and destruction procedures. The POM-3 was being used in 2022 during the Russian invasion of Ukraine. Another mine that exploits the flaws of EMI mine detection methods is the PFM-1 anti-personnel landmine (see FIG. 4). This mine has a plastic body and a small metal fuse. They can be dropped in large quantities from helicopters and airplanes or fired from mortars. Many PFM-1 landmines were used during the Soviet Invasion of Afghanistan. There is also evidence that these mines are being used in the 2022 Russian invasion of Ukraine.

As such, there remains a need for improved methods and systems of detecting and identifying explosives, such landmines and unexploded ordnance (UXO) on the surface.

SUMMARY OF THE INVENTION

Accordingly, the present invention is directed to systems and methods for detecting and identifying explosives on the ground, and more specifically systems and methods for detecting and identifying landmines and unexploded ordnance (UXO) on the surface.

As such, one aspect of the present invention provides a system for detecting and identifying explosives in a target area using an unmanned aerial vehicle (UAV) comprising:
- a UAV adapted to comprise an imaging device suitable to capture image data and a transmission component capable of transmitting said image data to a control system;
- an explosives detection and identification processing module comprising the control system suitable to receive and process the image data transmitted from the UAV, and wherein the module comprises a machine-readable medium having instructions stored thereon for execution by a processor to perform a method comprising the steps of:
  - storing the image data received from the UAV on the machine-readable medium;
  - processing the image data to generate images of a training area with known explosives;
  - fusing the images of the training area, e.g., with photogrammetry, to generate an orthomosaic image representative of the training area with the explosives;
  - analyzing one or more split images derived from the orthomosaic image using image processing algorithms, computer machine learning, computer vision machine learning (CVML), and/or an artificial neural network (e.g., convolutional neural network (CNN)) trained to detect patterns or predefined objects to generate a training model for automating the detection of explosives;
  - identifying and labelling the explosives in the training area in the orthomosaic image to refine the training model; and
  - applying the refined training model to a target area to predict the location of unknown explosives in the target area by comparing trained orthomosaic image data from the target area to previously generated orthomosaic image data from training area,
  - such that the system is suitable for detecting and identifying explosives in the target area using the unmanned aerial vehicle (UAV).

Another aspect of the present invention provides an explosives detection and identification processing module comprising the control system suitable to receive and process the image data transmitted from an unmanned aerial vehicle (UAV), and wherein the module comprises a machine-readable medium having instructions stored thereon for execution by a processor to perform a method comprising the steps of:
- storing the image data received from a UAV on the machine-readable medium;
- processing the image data to generate images of a training area with known explosives;
- fusing the images of the training area, e.g., with photogrammetry, to generate an orthomosaic image representative of the training area with the explosives;
- analyzing one or more split images derived from the orthomosaic image using image processing algorithms, computer machine learning, computer vision machine learning (CVML), and/or an artificial neural network (e.g., convolutional neural network (CNN)) trained to detect patterns or predefined objects to generate a training model for automating the detection of explosives;
- identifying and labelling the explosives in the training area in the orthomosaic image to refine the training model; and
- applying the refined training model to a target area to predict the location of unknown explosives in the target area by comparing trained orthomosaic image data from the target area to previously generated orthomosaic image data from training area,
- such that the module is suitable for detecting and identifying explosives in the target area using the unmanned aerial vehicle (UAV).

Another aspect of the present invention provides a method for detecting and identifying explosives in a target area using an unmanned aerial vehicle (UAV), the method comprising the steps of:

storing the image data received from a UAV on a machine-readable medium;

processing the image data to generate images of a training area with known explosives;

fusing the images of the training area, e.g., with photogrammetry, to generate an orthomosaic image representative of the training area with the explosives;

analyzing one or more split images derived from the orthomosaic image using image processing algorithms, computer machine learning, computer vision machine learning (CVML), and/or an artificial neural network (e.g., convolutional neural network (CNN)) trained to detect patterns or predefined objects to generate a training model for automating the detection of explosives;

identifying and labelling the explosives in the training area in the orthomosaic image to refine the training model; and applying the refined training model to a target area to predict the location of unknown explosives in the target area by comparing trained orthomosaic image data from the target area to previously generated orthomosaic image data from training area, such that the method is suitable for detecting and identifying explosives in the target area using the unmanned aerial vehicle (UAV).

BRIEF DESCRIPTION OF THE DRAWINGS

Advantages of the present systems, modules and related methods, will be apparent from the following detailed description, which description should be considered in combination with the accompanying figures, which are not intended to limit the scope of the invention in any way.

The present disclosure is described with reference to the following Figures. The same numbers are used throughout the Figures to reference like features and like components.

Figure 1:
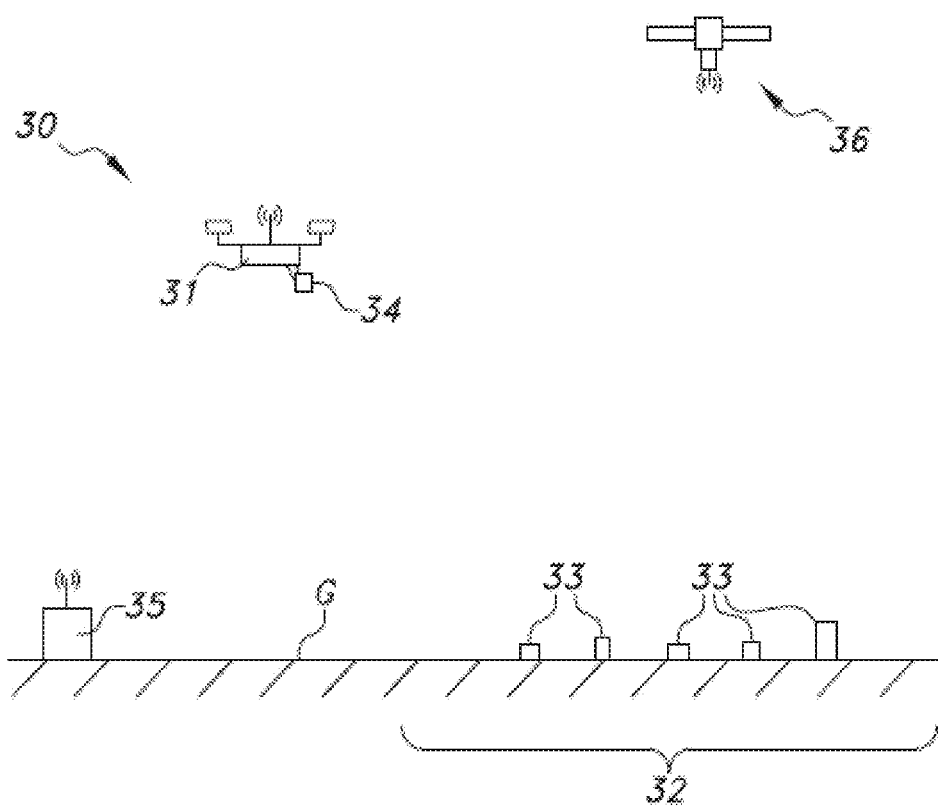
FIG. 1 a schematic diagram of an example system according to the present disclosure

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

DETAILED DESCRIPTION OF THE INVENTION

The present invention is directed to systems and methods for detecting and identifying explosives on the ground, and more specifically systems and methods for detecting and identifying landmines and unexploded ordnance (UXO) on the surface.

The present invention, including systems, processing system modules, and related methods will be described with reference to the following definitions that, for convenience, are set forth below. Unless otherwise specified, the below terms used herein are defined as follows:

I. Definitions

As used herein, the term "a," "an," "the" and similar terms used in the context of the present invention (especially in the context of the claims) are to be construed to cover both the singular and plural unless otherwise indicated herein or clearly contradicted by the context.

As used herein, the language "application programming interface" or "API" are art-recognized, and used interchangeably, to describe a type of software interface, offering a service to other pieces of software, i.e., a way for two or more computer programs to communicate with each other. In contrast to a user interface, which connects a computer to a person, an application programming interface connects computers or pieces of software to each other. It is not intended to be used directly by a person (the end user) other than a computer programmer who is incorporating it into the software. An API is often made up of different parts which act as tools or services that are available to the programmer. A program or a programmer that uses one of these parts is said to call that portion of the API. The calls that make up the API are also known as subroutines, methods, requests, or endpoints. An API specification defines these calls, meaning that it explains how to use or implement them.

The term "explosives" is used herein to describe landmines and unexploded ordnance, also referred to as UXO or LUXO.

The term "interfacing" is art-recognized, and is used herein to describe the means of communication between two entities, for example a system/tool and user data entry. In certain embodiments, the interfacing may be bi-directional. In other embodiments, the interfacing may be uni-directional. In particular embodiments, such interfacing may be achieved through a graphical user interface.

The language "machine-readable medium" is art-recognized, and describes a medium capable of storing data in a format readable by a mechanical device (rather than by a human). Examples of machine-readable media include magnetic media such as magnetic disks, cards, tapes, and drums, punched cards and paper tapes, optical disks, barcodes, magnetic ink characters, and solid state devices such as flash-based, SSD, etc. Machine-readable medium of the present invention are non-transitory, and therefore do not include signals per se, i.e., are directed only to hardware storage medium. Common machine-readable technologies include magnetic recording, processing waveforms, and barcodes. In particular embodiments, the machine-readable device is a solid state device. Optical character recognition (OCR) can be used to enable machines to read information available to humans. Any information retrievable by any form of energy can be machine-readable. Moreover, any data stored on a machine-readable medium may be transferred by streaming over a network. In a particular embodiment, the machine readable medium is a network server disk, e.g., an internet server disk, e.g., a disk array. In specific embodiments, the machine-readable medium is more than one network The language "orthomosaic image" is art-recognized and used herein to describe a composite image including some or all of the images captured by UAV. The images are "fused" together and edited so that the orthomosaic image is generated and the space in the image represents real distances. The orthomosaic image is generated by a module or technique. An example known module that is capable to generating the orthomosaic image is a Pix4Dmapper. In certain embodiments, the module that generates the orthomosaic image can also generate an associated world file that contains data corresponding to the location and scale of the orthomosaic image in real space.

The term "user" is used herein to describe any person that interfaces with the tools of the present invention described herein through electronic means, e.g., computer or mobile device. Such user may be credentialed or non-credentialed, and which may afford certain access rights in the interface based on such status.

The language "user interface" is used herein to describe the graphical user interface (GUI), e.g., which allows a user to interface with the application programming interface (API), and enter data using interface components such as buttons, text fields, check boxes, etc.

II. Explosive Detection and Identification of the Invention

The present invention uses UAVs adapted with the miniaturized optical and geophysical sensors, and visual and thermal sensors to detect and locate explosives, or LUXO to assist in humanitarian mine action (HMA) to thereby contribute to the sector through rapid low-cost data acquisition over large areas; reducing costs, dangers, and time associated with surveying contaminated areas. The resulting increased production of and accessibility to data from UAVs, and the describe capability of analyzing these large datasets avoids delays in processing the data. In contrast to manual analysis, which can be time-consuming, subjective, and inconsistent, the systems and methods of the present invention implement processing the datasets using computer and machine learning to aid in identifying the presence of mines in UAV surveys. This allows stakeholders to more intelligently plan HMA activities. This methodology will also help reduce the search area size of contaminated areas and provide key information on which areas to prioritize clearance activities.

A. Method of Detecting and Identifying Explosives of the Present Invention

As such, one embodiment of the present invention provides a method for detecting and identifying explosives in a target area using an unmanned aerial vehicle (UAV), the method comprising the steps of:
  storing the image data received from a UAV on a machine-readable medium;
  processing the image data to generate images of a training area with known explosives;
  fusing the images of the training area, e.g., with photogrammetry, to generate an orthomosaic image representative of the training area with the explosives;
  analyzing one or more split images derived from the orthomosaic image using image processing algorithms, computer machine learning, computer vision machine learning (CVML), and/or an artificial neural network (e.g., convolutional neural network (CNN)) trained to detect patterns or predefined objects to generate a training model for automating the detection of explosives;
  identifying and labelling the explosives in the training area in the orthomosaic image to refine the training model; and
  applying the refined training model to a target area to predict the location of unknown explosives in the target area by comparing trained orthomosaic image data from the target area to previously generated orthomosaic image data from training area,
  such that the method is suitable for detecting and identifying explosives in the target area using the unmanned aerial vehicle (UAV).

In certain embodiments of the present invention, the location of the predicted explosives are displayed to the user via an output device selected from a mobile smart phone or a touchscreen tablet.

In certain embodiments of the present invention, the location of the predicted explosives are displayed to the user via an output device selected from a web application.

Figure 3:
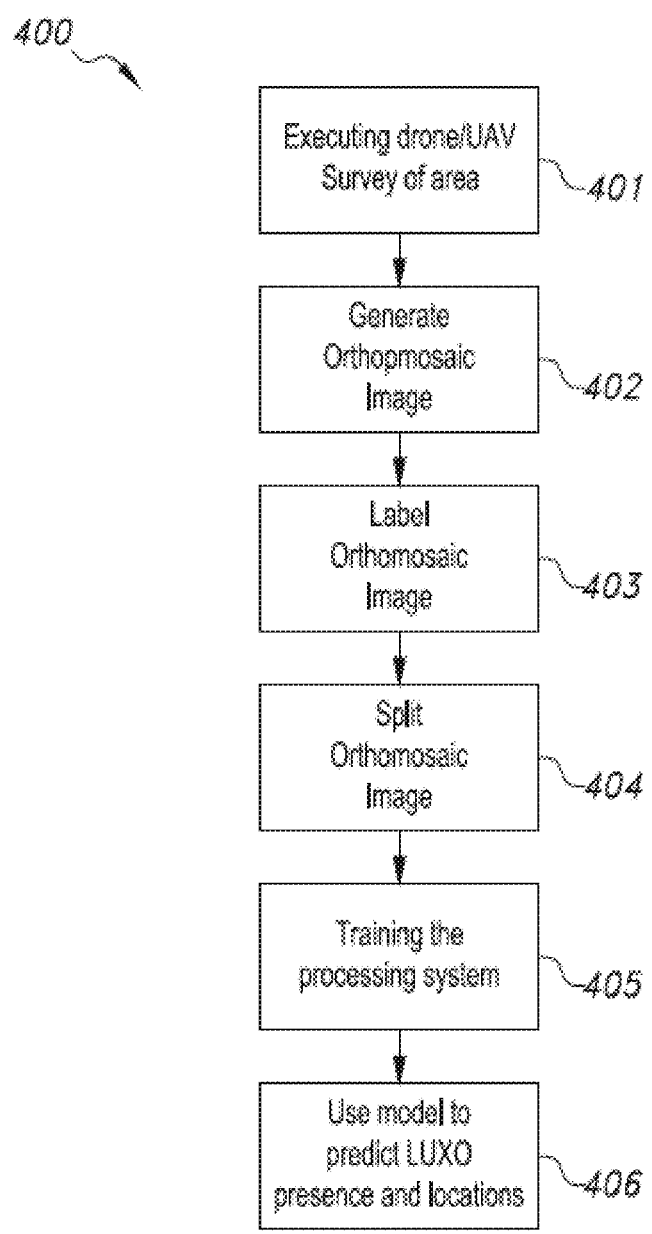
FIG. 3 is an example method of the present disclosure.
Figure 4:
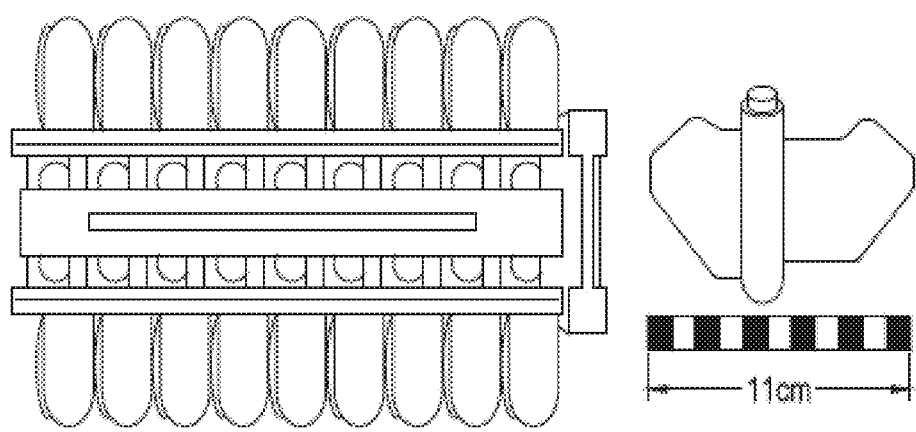
FIG. 4 is a top-down view and a side-view of an example PFM-1 anti-personnel landmine.

Referring now to FIG. 3, an example method for detecting, locating, and/or identifying LUXO on or in predetermined area 32 is depicted. The example depicted method is described further herein below.

i. Storing Image Data Received from UAV

The methods of detecting and identifying explosives in a target area using an unmanned aerial vehicle (UAV), comprises the step of storing the image data received from a UAV on a machine-readable medium.

In certain embodiments of the present invention, the image data collection by aerial vehicle (e.g., UAV) occurs over multiple passes of the training area, e.g., collecting the data by multiple passes in multiple conditions. In certain embodiments, the data is collected using multiple image collection techniques and/or imaging devices. For example, UAV 34 may be flown several times in one day or over the course of several days over the training area to thereby generate different image data having different lighting and other environmental conditions.

In certain embodiments of the invention, the image data and datasets of the same area under different lighting and environmental conditions can be used by the processing system 111 to detect and identify the LUXO as noted above at 401-403 efficiency increases. In certain examples, one orthomosaic image of the area 32 is labeled with rough bounding box labels for orthomosaic images of the area. The location of ground control points set by the user is used to further refine the location of the bounding box labels. These bounding box labels will however usually be slightly shifted from the location of the mine in the orthomosaic image. Note that in this case it is still necessary to go process the orthomosaic image as noted above with respect to 403 to apply the labels and/or adjust the labels (e.g., bounding boxes) to accurately outline the objects of interest.

In certain embodiments, at 401, the UAV 31 is the flown near and/or over the area 32 to image the ground G within the area 32 with the imaging device 34. In one specific example, the UAV 31 is flown over areas 32 believed or known to be contaminated with LUXO. The flight path of the UAV 31 over the area 32 to thereby properly image the area 32 can be dependent on flight conditions (e.g., temp, wind, precipitation), imaging device 34 specifications (e.g., pixel, zoom), and/or UAV 31 specifications (e.g., air speed, operation duration between refueling/recharging). The flight path may be communicated to the UAV 31 by the user via the remote control device 35, selected by the user based on analysis of image data relayed to the control system 100 to conform with predetermined image requirements for the area (e.g., percent overlap between adjacent images). In one non-limiting example, the UAV 31 is flown along a predetermined rectangular flight path at an elevation of 8.0-12.0 meters about the ground G. In this specific example, the UAV 31 flies at a speed of 1.0 meters per second and takes an image/picture of a portion of the area 32 every 1.50 second such that the overlap between adjacent images is 80.0-85.0% of front and side overlap between transects. The distance between the UAV 31 and the ground G can vary and the system 30. Note that UAV 31 may log and communicate GPS data as it flies along the flight path and/or tag each captured image the corresponding GPS data. In certain examples, the images are tagged with GPS data based on internal drone GPS devices.

In other examples, the images are tagged with GPS data based on ground control points surrounding the area 32. For example, the GPS data may be based on a global navigation satellite system (GNSS) like a Trimble Zephyr 3.

In certain embodiments of the present invention, the image data collected from the UAV is multi spectral data.

In certain embodiments of the present invention, the transmission of the image data to the control system is wired or wireless.

ii. Processing the Image Data to Generate Images of Training Area

The methods of detecting and identifying explosives in a target area using an unmanned aerial vehicle (UAV), comprises the step of processing the image data to generate images of a training area with known explosives.

In certain embodiments of the invention, the image data from the imaging device 34 is provided to the processing system 111 that may include one or more image processors that process the data to generate an image, compare the image data to previously generated images, identify similarities, differences, and/or patterns in the data or images, and/or detect objects, such as LUXO 33, within the data or images. In certain examples, the processing system 111 utilizes tools on the images data to determine feature of the objects (e.g., LUXO 33) imaged by the imaging device 34. The tools can include obtaining coordinates of objects and boundaries. In certain examples, the processing system 111 and/or the control system 100 generally, incorporates image processing algorithms, techniques, modules, computer machine learning, computer vision machine learning (CVML), and/or an artificial neural network trained to detect patterns or predefined objects. In certain examples, the processing system 111 can include artificial intelligence systems (e.g., IBM's Watson Artificial Intelligence). In certain examples, processing system 111 includes a machine learning model based on an architecture called Faster R-CNN implemented by the OpenMMLab in a project called MMDetection. In certain examples, the processing system 111 includes using one or more of the following methodologies/tools: TensorFlow, Keras, Python, OpenCV, neural network, Deep Learning, and/or Computer Vision.

Note that in certain examples the example method can include the steps of conducting a survey of an known area 34 with known LUXO 33 present in the area 34 to thereby generate image data similar to the image data described above at 401 and further process the image data from the known area 34 to generate an orthomosaic image similar to orthomosaic image generated above at 402. As such, the orthomosaic images and related to the known area with known LUXO 33 forms a known dataset for a starting point for the processing system 111 to process other additional datasets relative to new areas 34 with known or unknown areas with unknown LUXO 33. As such, the datasets (e.g., the dataset of the known area with the known LUXO and the dataset of another areas with unknown LUXO) build on each other and help to train processing systems (e.g., artificial intelligence, neural networks, computer learning) to detect and identify LUXO in unknown locations as the system 30 is subsequently used to locate LUXO additional areas 32.

iii. Fusing Images of Training Area to Generate Orthomosaic Image

The methods of detecting and identifying explosives in a target area using an unmanned aerial vehicle (UAV), comprises the step of fusing the images of the training area, e.g., with photogrammetry, to generate an orthomosaic image representative of the training area with the explosives.

In certain embodiments of the invention, the fused image includes both image data and data from other sources, including GPS and map data.

iv. Analyzing Split Images Derived From Orthomosaic Image

The methods of detecting and identifying explosives in a target area using an unmanned aerial vehicle (UAV), comprises the step of analyzing one or more split images derived from the orthomosaic image using image processing algorithms, computer machine learning, computer vision machine learning (CVML), and/or an artificial neural network (e.g., convolutional neural network (CNN)) trained to detect patterns or predefined objects to generate a training model for automating the detection of explosives.

In certain embodiments of the present invention, the output of this step is a plurality of the split orthomosaic images with a unique naming convention so the location of each orthomosaic image relative to the larger, unsplit orthomosaic image can be determined and/or an updated annotation file.

In certain embodiments of the present invention, the orthomosaic image is split into smaller file size and/or image size orthomosaic image which are then processed by the processing system. For example, the processing system 111 processing the split orthomosaic images by inputting the split orthomosaic images via a neural network or machine learning model. In certain embodiments, the processing system 111 may only process a maximum accepted image size that is smaller than un-split orthomosaic image. In particular embodiments, the processing system 111 can include a technique that splits the labeled orthomosaic image as noted above at 403 and generates data that corresponds to the location of the split orthomosaic image relative to the un-split orthomosaic image as noted above. The processing system 111 in this example may also generate annotation file for each corresponding split orthomosaic image. Note in certain example, splitting the orthomosaic images involves cropping images with a user-defined percentage of overlap to other adjacent split orthomosaic images so that split orthomosaic images are truncated in one image and will be complete in a neighboring image. For instance, this overlapping feature of the processing system 111 can include smart-cropping so that the user-defined crop size minimally grows or shrinks to make sure every cropped image for each orthomosaic image is of uniform size.

In certain embodiments of the present invention, once the data is split and placed in the correct folder structure, the processing system 111 waits for an input command from the user to begin the training. When the processing system 111 completes the training session with one or more datasets or image data a completed training file is outputted and stored to the memory system 112 that a model dataset of the classes of LUXO it was trained to predict encoded into it. This model dataset is used to predict the presence and location of UXO in other subsequent files, image data, and/or datasets at 406.

v. Identifying And Labelling Explosives In Training Area

The methods of detecting and identifying explosives in a target area using an unmanned aerial vehicle (UAV), comprises the step of identifying and labelling the explosives in the training area in the orthomosaic image to refine the training model.

In certain embodiments of the invention, the step of labelling the orthomosaic image includes marking with indicia selected from the group consisting of boxes, geometric systems, alphanumerical text, graphics, color, and any combination thereof. In certain embodiments, each explosive detected and identified on the labelled orthomosaic image is assigned a quality grade metric. Note that in certain embodiments, after the orthomosaic image is labeled as noted above at 403 with an additional module of the processing system 111 to thereby assign a quality grade metric (e.g., good, medium, bad), e.g., to each bounding box label boxes and/or the object detected and identified by the processing system 111. As such, the dataset can be sorted by the quality grade metric such that the user and/or the control system 100 can remove or relabel the quality grade metric. The orthomosaics, annotations and world files may be placed in a private GitHub repository.

In certain embodiments of the invention, the processing system 111 applies labels to the orthomosaic image generated at 402. The labels for the object identified by the processing system 111 are added to the orthomosaic image and can be any suitable indicia such as boxes, geometric systems, alphanumerical text, graphics, color, and the like.

In certain embodiments of the invention, the method further comprises the step of generating an associated world file that contains training area data corresponding to the location and scale of the orthomosaic image in real space.

In certain embodiments of the invention, the method further comprises the step of producing an annotation file that contains a list of all labeled explosives and corresponding munition type and GPS location data in the training area.

In another example, the processing system 111 executes another script to overlay the predicted locations of LUXO, their class and confidence score, back onto the orthomosaic images from which the predictions were taken. This creates a highly detailed aerial map of a region showing specifically the type and level of contamination in a region.

In certain embodiments of the present invention, the processing system 111 includes an interface for the user to manually review all the predicted locations of the LUXO. In this examples, the processing system 111 generates predicted boxes and labels overlain onto the orthomosaic images so a user can see the predicted box and judge if contained in that box is really what the machine predicted. Using the predicted location of the LUXO, the user can quickly and efficiently mark all the predictions they believe to be false alarms so what remains is a list of vetted coordinate predictions of UXO that Explosive Ordnance Disposal (EOD) teams can investigate.

vi. Applying Refined Training Model to Target Area

The methods of detecting and identifying explosives in a target area using an unmanned aerial vehicle (UAV), comprises the step of applying the refined training model to a target area to predict the location of unknown explosives in the target area by comparing trained orthomosaic image data from the target area to previously generated orthomosaic image data from training area.

In certain embodiments of the present invention, the step of applying the refined training model to the target area comprises the steps of:

storing the target area image data on the machine-readable medium;

processing the target area image data to generate images of the target area with unknown explosives;

fusing the images of the target area to generate an orthomosaic image representative of the target area with the unknown explosives;

analyzing one or more split images derived from the orthomosaic image using the refined training model with image processing algorithms, computer machine learning, computer vision machine learning (CVML), and/or an artificial neural network (e.g., convolutional neural network (CNN)) to predict the location of unknown explosives in the target area by comparing trained orthomosaic image data from the target area to previously generated orthomosaic image data from training area; and identifying and labelling the explosives in the target area in the orthomosaic image. In certain embodiments, the data obtained in the identification and labelling of the explosives in the target area is used to further refine the training model to detect and identify unknown explosives.

In certain embodiments of the present invention, the image data collection by aerial vehicle (e.g., UAV) occurs over multiple passes of the training area, e.g., collecting the data by multiple passes in multiple conditions. In certain embodiments, the data is collected using multiple image collection techniques and/or imaging devices. For example, UAV 34 may be flown several times in one day or over the course of several days over the target area 32 to thereby generate different image data (see at 401) having different lighting and other environmental conditions.

In certain embodiments of the invention, the image data and datasets of the same area under different lighting and environmental conditions can be used by the processing system 111 to detect and identify the LUXO as noted above at 401-403 efficiency increases. In certain examples, one orthomosaic image of the area 32 is labeled with rough bounding box labels for orthomosaic images of the area. The location of ground control points set by the user is used to further refine the location of the bounding box labels. Note that in this case it is still necessary to go process the orthomosaic image as noted above with respect to 403 to apply the labels and/or adjust the labels (e.g., bounding boxes) to accurately outline the objects of interest.

In certain embodiments, at 401, the UAV 31 is the flown near and/or over the area 32 to image the ground G within the area 32 with the imaging device 34. In one specific example, the UAV 31 is flown over areas 32 believed or known to be contaminated with LUXO. The flight path of the UAV 31 over the area 32 to thereby properly image the area 32 can be dependent on flight conditions (e.g., temp, wind, precipitation), imaging device 34 specifications (e.g., pixel, zoom), and/or UAV 31 specifications (e.g., air speed, operation duration between refueling/recharging). The flight path may be communicated to the UAV 31 by the user via the remote control device 35, selected by the user based on analysis of image data relayed to the control system 100 to conform with predetermined image requirements for the area (e.g., percent overlap between adjacent images). In one non-limiting example, the UAV 31 is flown along a predetermined rectangular flight path at an elevation of 8.0-12.0 meters about the ground G. In this specific example, the UAV 31 flies at a speed of 1.0 meters per second and takes an image/picture of a portion of the area 32 every 1.50 second such that the overlap between adjacent images is 80.0-85.0% of front and side overlap between transects. The distance between the UAV 31 and the ground G can vary and the system 30. Note that UAV 31 may log and communicate GPS data as it flies along the flight path and/or tag each captured image the corresponding GPS data. In certain examples, the images are tagged with GPS data based on internal drone GPS devices. In other examples, the images are tagged with GPS data based on ground control points surrounding the area 32. For example, the GPS data may be based on a global navigation satellite system (GNSS) like a Trimble Zephyr 3.

In certain embodiments of the present invention, the image data collected from the UAV is multi spectral data.

In certain embodiments of the present invention, the transmission of the image data to the control system is wired or wireless.

In certain embodiments of the present invention, the step of labelling the orthomosaic image includes marking with indicia selected from the group consisting of boxes, geometric systems, alphanumerical text, graphics, color, and any combination thereof. In certain embodiments, each explosive detected and identified on the labelled orthomosaic image is assigned a quality grade metric. Note that in certain embodiments, after the orthomosaic image is labeled as noted above at 403 with an additional module of the processing system 111 to thereby assign a quality grade metric (e.g., good, medium, bad), e.g., to each bounding box label boxes and/or the object detected and identified by the processing system 111. As such, the dataset can be sorted by the quality grade metric such that the user and/or the control system 100 can remove or relabel the quality grade metric. The orthomosaics, annotations and world files may be placed in a private GitHub repository.

In certain embodiments of the invention, the method further comprises the step of generating an associated world file that contains target area data corresponding to the location and scale of the orthomosaic image in real space.

In certain embodiments of the invention, the method further comprises the step of producing an annotation file that contains a list of all labeled explosives and corresponding munition type and GPS location data in the target area.

In another example, the processing system 111 executes another script to overlay the predicted locations of LUXO, their class and confidence score, back onto the orthomosaic images from which the predictions were taken. This creates a highly detailed aerial map of a region showing specifically the type and level of contamination in a region.

B. Explosives Detection And Identification Processing Module of the Present Invention The methods of the present invention may be utilized and implemented as a processing system module or processing system 111. As such, one embodiment of the present invention provides an explosives detection and identification processing module comprising the control system suitable to receive and process the image data transmitted from an unmanned aerial vehicle (UAV), and wherein the module comprises a machine-readable medium having instructions stored thereon for execution by a processor to perform a method comprising the steps of:

storing the image data received from a UAV on the machine-readable medium;

processing the image data to generate images of a training area with known explosives;

fusing the images of the training area, e.g., with photogrammetry, to generate an orthomosaic image representative of the training area with the explosives;

analyzing one or more split images derived from the orthomosaic image using image processing algorithms, computer machine learning, computer vision machine learning (CVML), and/or an artificial neural network (e.g., convolutional neural network (CNN)) trained to detect patterns or predefined objects to generate a training model for automating the detection of explosives;

identifying and labelling the explosives in the training area in the orthomosaic image to refine the training model; and applying the refined training model to a target area to predict the location of unknown explosives in the target area by comparing trained orthomosaic image data from the target area to previously generated orthomosaic image data from training area, such that the module is suitable for detecting and identifying explosives in the target area using the unmanned aerial vehicle (UAV).

In certain embodiments of the invention, the control system is suitable to receive and process positioning data from a GPS sensor component and such data is fused into the orthomosaic image.

In certain embodiments of the invention, the image data and datasets of the same area under different lighting and environmental conditions can be used by the processing system 111 to detect and identify the LUXO as noted above at 401-403 efficiency increases. In certain examples, a first script (e.g., list of python commands that is executed based on module of the processing system 111 and/or stored on the memory system 112) to label one orthomosaic image of the area 32 with rough bounding box labels for orthomosaic images of the area. A second script uses the location of ground control points set by the user further refine the location of the bounding box labels. These bounding box labels will however usually be slightly shifted from the location of the mine in the orthomosaic image. Note that in this case, it is still necessary to go process the orthomosaic image with the processing system 111 as noted above with respect to 403 to apply the labels and/or adjust the labels (e.g., bounding boxes) to accurately outline the objects of interest.

In certain embodiments, the images of the area 32 are captured by the UAV and communicated to the control system (e.g., during or after the flight of the UAV 31, wirelessly or wired connection between the UAV and port on the remote control device that is in communication with the control system 100). In certain examples, the processing systems 111 process the image data using one or more methodology, tool, model, or the like. In certain examples, the processing system 111 generates an orthophoto or orthomosaic image of the image data generated by the UAV at 402.

In certain embodiments of the present invention, after the orthomosaic image is split, the datasets and/or split images are stored in the memory system 112, and may include the split orthomosaic images with corresponding annotation files (containing the labels), world files (containing the real-world spatial information), and/or one annotation file describing all the labelled munitions in those images and a metadata file describing the crop size and overlap size taken for each orthomosaic (this is information is important in locating coordinates in the split images in real space).

In one specific non-limiting example, the labels applied to the orthomosaic image are rectangular boxes with alphanumerical text that correspond to a LUXO dataset stored in the memory system 112. In certain examples, the processing system 111 uses machine learning model or neural network to determine the LUXO in the orthomosaic image or split orthomosaic images. In certain examples, datasets and the orthomosaic image or split orthomosaic images are stored in the memory system 112. The labels applied can include the corresponding munition class or name so the processing system 111 can form and/or continue to refine the general model of the specific munition as additional areas 34 are surveyed as noted at 401. As such, in certain examples, the processing system 111 (e.g., the computer learning model or the neural network) is "trained" or "learns" to detect and label similar munition in different surveyed areas 34. The processing system 111 is also capable of producing an annotation file that contains a list of all labeled LUXO and corresponding data (e.g., munition type such as projectile, grenade, or anti-personnel landmine; GPS location data).

In certain embodiments, once the processing system 111 (e.g., machine learning model, neural network) is trained, the control system 110 includes a trained processing system 111 (e.g., machine learning model) and either labelled data with which to evaluate the performance of the model is processed by the control system 100 or unlabeled image data from new areas 32 on which to generate predictions of LUXO presence and locations is generated at 406. The first step towards these ends is to discover at which epoch the model performed the best. The training data is fed through the processing system 111 in phases called epochs. In each epoch, the training data is fed into the processing system 111 the memory system 112 in randomized batches to increase variability and efficiency. With each epoch, the model gets better and better at identifying the exact objects of interest in the training set but that may mean that it is getting worse at forming a generalized enough model to identify the images in the testing set, data it is not trained on. When the processing system 111 "sees" an object of a particular size, color and orientation, it is only trained to detect objects of that size, color and orientation. It is important to train the one or more aspect of the processing system 111 on a large diversity of training data but not for too many epochs, or else it will become specialized at identifying the images in the training set and will not be able to detect munitions in any other data.

In certain embodiments of the present invention, the processing system 111 is further configured to use another technique such as a script to output graphs that make it very easy to identify the epoch at which the model performs best. The trained model from this epoch is then used to evaluate the performance of this model against the testing set to assess how accurate this model will be at identifying UXO in unknown locations. Graphs and spreadsheets are outputted from the processing system assess the accuracy of the model. The accuracy is calculated on the level of the orthomosaic images. This means the processing system 111 determines the location of where the predicted boxes would be in its respective orthomosaic image(s). This provides the user with helpful statistics about how many objects were detected correctly, incorrectly, and missed in each orthomosaic image.

In certain embodiments of the present invention, the processing system 111 executes a script to calculate and output the real-life coordinate predictions of the predicted LUXO objects.

In another examples, the processing system 111 executes another script to overlay the predicted locations of LUXO, their class and confidence score, back onto the orthomosaic images from which the predictions were taken. This creates a highly detailed aerial map of a region showing specifically the type and level of contamination in a region.

C. Systems for Detecting and Identifying Explosives of the Present Invention The methods and processing modules of the present invention may serve as components of and be implemented as a system, including additional components such as, the UAV, remote control device, output device, and/or a GPS sensor component. As such, another embodiment of the present invention is directed to a system for detecting and identifying explosives in a target area using an unmanned aerial vehicle (UAV) comprising:

a UAV adapted to comprise an imaging device suitable to capture image data and a transmission component capable of transmitting said image data to a control system;

an explosives detection and identification processing module comprising the control system suitable to receive and process the image data transmitted from the UAV, and wherein the module comprises a machine-readable medium having instructions stored thereon for execution by a processor to perform a method comprising the steps of:

storing the image data received from the UAV on the machine-readable medium;

processing the image data to generate images of a training area with known explosives;

fusing the images of the training area, e.g., with photogrammetry, to generate an orthomosaic image representative of the training area with the explosives;

analyzing one or more split images derived from the orthomosaic image using image processing algorithms, computer machine learning, computer vision machine learning (CVML), and/or an artificial neural network (e.g., convolutional neural network (CNN)) trained to detect patterns or predefined objects to generate a training model for automating the detection of explosives;

identifying and labelling the explosives in the training area in the orthomosaic image to refine the training model; and applying the refined training model to a target area to predict the location of unknown explosives in the target area by comparing trained orthomosaic image data from the target area to previously generated orthomosaic image data from training area, such that the system is suitable for detecting and identifying explosives in the target area using the unmanned aerial vehicle (UAV).

In certain embodiments of the invention, the system further comprises a GPS sensor component positioned on the UAV, suitable to capture positioning data and capable of transmitting said image data to the control system, wherein the control system is suitable to receive and process positioning data from the GPS sensor component and such data is fused into the orthomosaic image.

In certain embodiments of the invention, the imaging device is selected from the group consisting of a camera, visual-light sensor, multispectral sensor, a thermal sensor, and any combination thereof.

Figure 2:
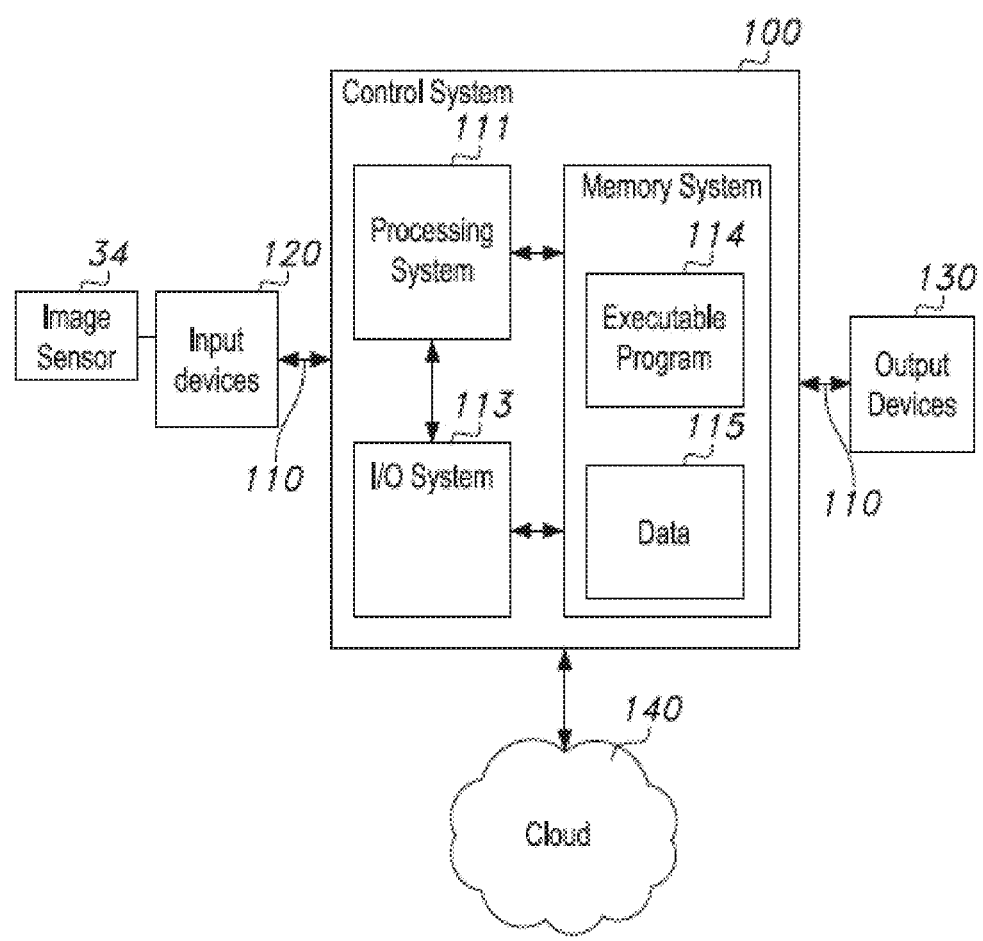
FIG. 2 is a schematic diagram of an example control system according to the present disclosure.

In certain embodiments, the UAV 31 is in communication with and is controlled by a remote control device 35. FIG. 1 depicts the remote control device 35 as a stationary unit located on the ground G, which can be operated by a user. In other examples, the remote control device 35 is a hand-transported module that can be carried by a user or ground vehicle. In still another example, the remote control device 35 is integrated into or attached to a mobile ground vehicle (e.g., tank, Humvee). The remote control device 35 and/or the UAV 31 can be in communication with and/or part of a control system 100 (described herein; see FIG. 2) to thereby transfer data between the UAV 31, the remote control device 35, and/or the control system 100. The remote control device 35 and/or the UAV 31 can also be in communication with mobile data/telephone network and/or satellites 36 such that data can be transferred to different components of the system 30 and global positioning data (e.g., GPS coordinates) can be determined.

In certain embodiments of the invention, the control system 100 communicates with each of the one or more components of the system 30 via a communication link 110, which can be any wired or wireless link. The control module 100 is capable of receiving information and/or controlling one or more operational characteristics of the system 30 and its various sub-systems by sending and receiving control signals via the communication links 110. In one example, the communication link 100 is a controller area network (CAN) bus; however, other types of links could be used. It will be recognized that the extent of connections and the communication links 110 may in fact be one or more shared connections, or links, among some or all of the components in the system 30. Moreover, the communication link 110 lines are meant only to demonstrate that the various control elements are capable of communicating with one another, and do not represent actual wiring connections between the various elements, nor do they represent the only paths of communication between the elements. Additionally, the system 30 may incorporate various types of communication devices and systems, and thus the illustrated communication links 110 may in fact represent various different types of wireless and/or wired data communication systems.

In certain embodiment of the invention, the control system 100 may be a computing system that includes a processing system 111, memory system 112, and input/output (I/O) system 113 for communicating with other devices, such as input devices 120 (such as the imaging device 34 or a GPS sensor/device) and output devices 130, either of which may also or alternatively be stored in a cloud 140. The processing system 111 loads and executes an executable program 114 from the memory system 112, accesses data 115 stored within the memory system 112, and directs the system 30 to operate as described in further detail herein.

In certain embodiments of the present invention, the machine-readable medium, or memory system 112, may comprise any storage media readable by the processing system 111 and capable of storing the executable program 114 and/or data 115. The memory system 112 may be implemented as a single storage device, or be distributed across multiple storage devices or sub-systems that cooperate to store computer readable instructions, data structures, program modules, or other data. The memory system 112 may include volatile and/or non-volatile systems, and may include removable and/or non-removable media implemented in any method or technology for storage of information. The storage media may include non-transitory storage media, including random access memory, read only memory, magnetic discs, optical discs, flash memory, virtual memory, and non-virtual memory, magnetic storage devices, or any other medium which can be used to store information and be accessed by an instruction execution system, for example.

In certain embodiments of the present invention, the processing system 111 may be implemented as a single microprocessor or other circuitry, or be distributed across multiple processing devices or sub-systems that cooperate to execute the executable program 114 from the memory system 112. Non-limiting examples of the processing system include general purpose central processing units, application specific processors, and logic devices.

In certain embodiments of the present invention, the location of the predicted LUXO are displayed to the user via an output device 130 such as a mobile smart phone, a touchscreen tablet, or web application. In certain embodiments, the processing system 111 executes a script to calculate and output the real-life coordinate predictions of the predicted LUXO objects. These coordinates can easily be viewed in any Geographic Information System (GIS) such as Google Earth Pro or QGIS. Along with the location of each predicted object is a predicted label for which class of ordnance it belongs to and a confidence score that represents how certain the machine is that there is a mine in this location.

Certain aspects of the present disclosure are described or depicted as functional and/or logical block components or processing steps, which may be performed by any number of hardware, software, and/or firmware components configured to perform the specified functions. For example, certain embodiments employ integrated circuit components, such as memory elements, digital signal processing elements, logic elements, look-up tables, or the like, configured to carry out a variety of functions under the control of one or more processors or other control devices. The connections between functional and logical block components are merely exemplary, which may be direct or indirect, and may follow alternate pathways.

EXEMPLIFICATION

Example 1

Exemplary Embodiment: Systems for Detecting and Identifying Explosives

An exemplary embodiment of the systems of the present invention is described herein below. Referring to FIG. 1, an example system 30 for detecting and locating landmines and other unexploded ordnance (UXO) (collectively referred to herein below as "LUXO"). As will be described further herein below, the present disclosure includes methods for utilizing a convolutional neural network (CNN) and/or a machine learning model to automate the detection of surface-lain LUXO from unpiloted-aerial-vehicle-based (UAV) imagery.

The system 30 generally includes a UAV 31 that is flown nearby and/or over a subject field or area 32 when LUXO 33 on or buried in the ground G. The UAV 31 can be any suitable aerial device capable of flying near or over the area 32 and imagining the areas 32 (described further herein). In certain examples, the UAV 31 is a commercial quadcopter or hexcopter adapted to achieve the goals of the present invention with an imaging device 34 such as a camera, visual-light sensor, multi-spectral sensor, and/or thermal sensor. In specific examples, the UAV is an adapted aerial drone such as DJI Matrice 600, DJI Phantom 4, or DJI Mavic 2 Enterprise Dual.

Figure 5:
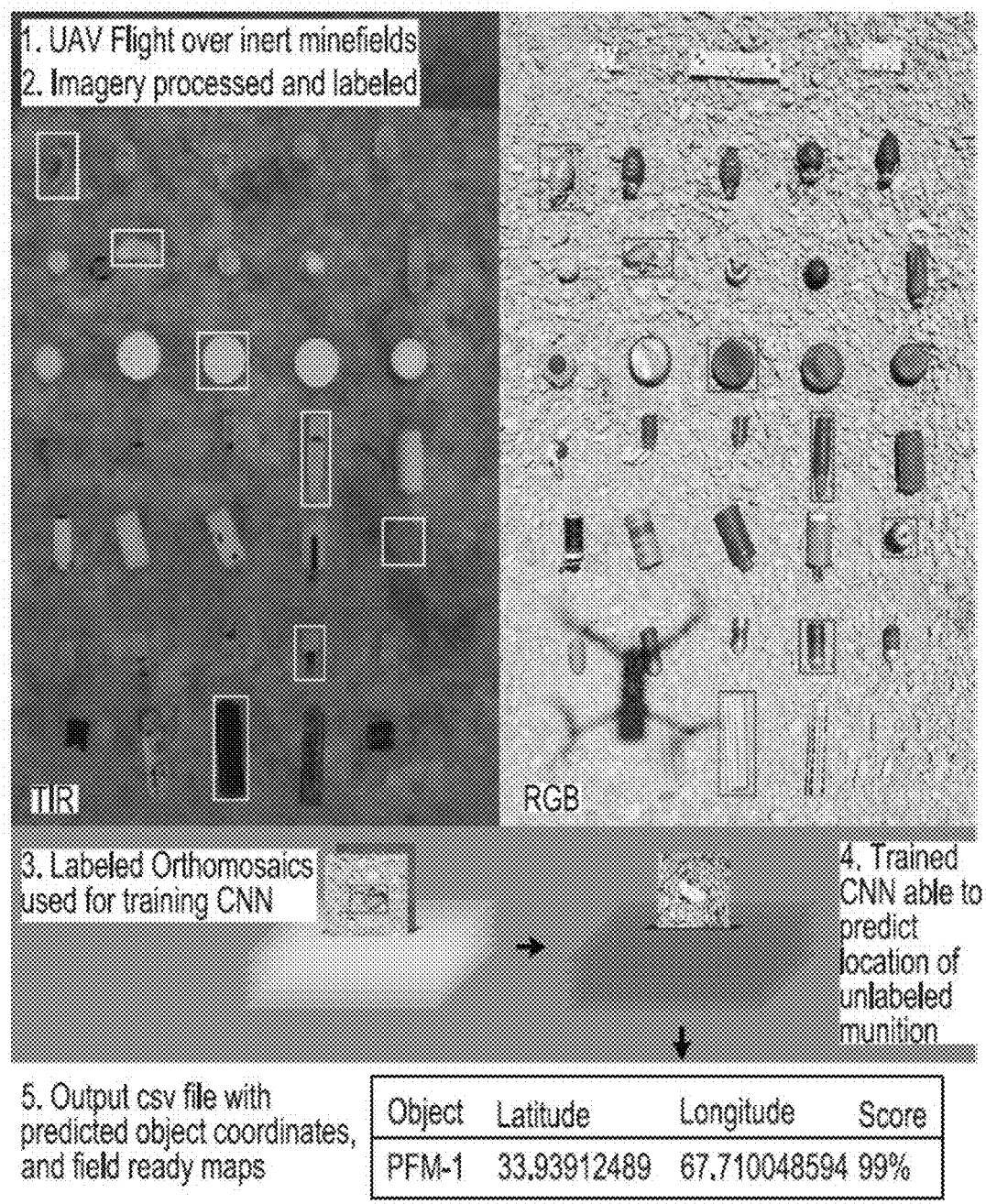
FIGS. 5-7 depict graphical representations of example image data and steps of the method of FIG. 3 according to the present disclosure.
Figure 6:
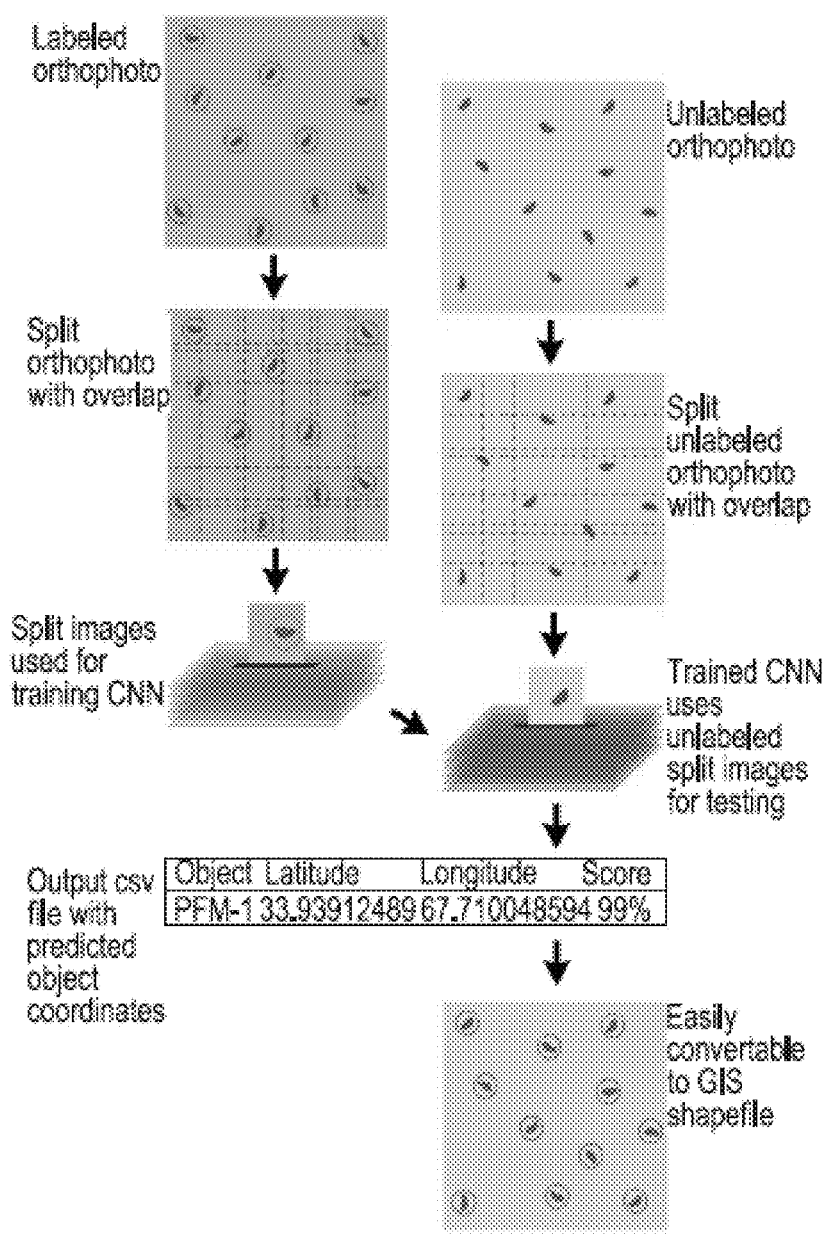
Figure 7:
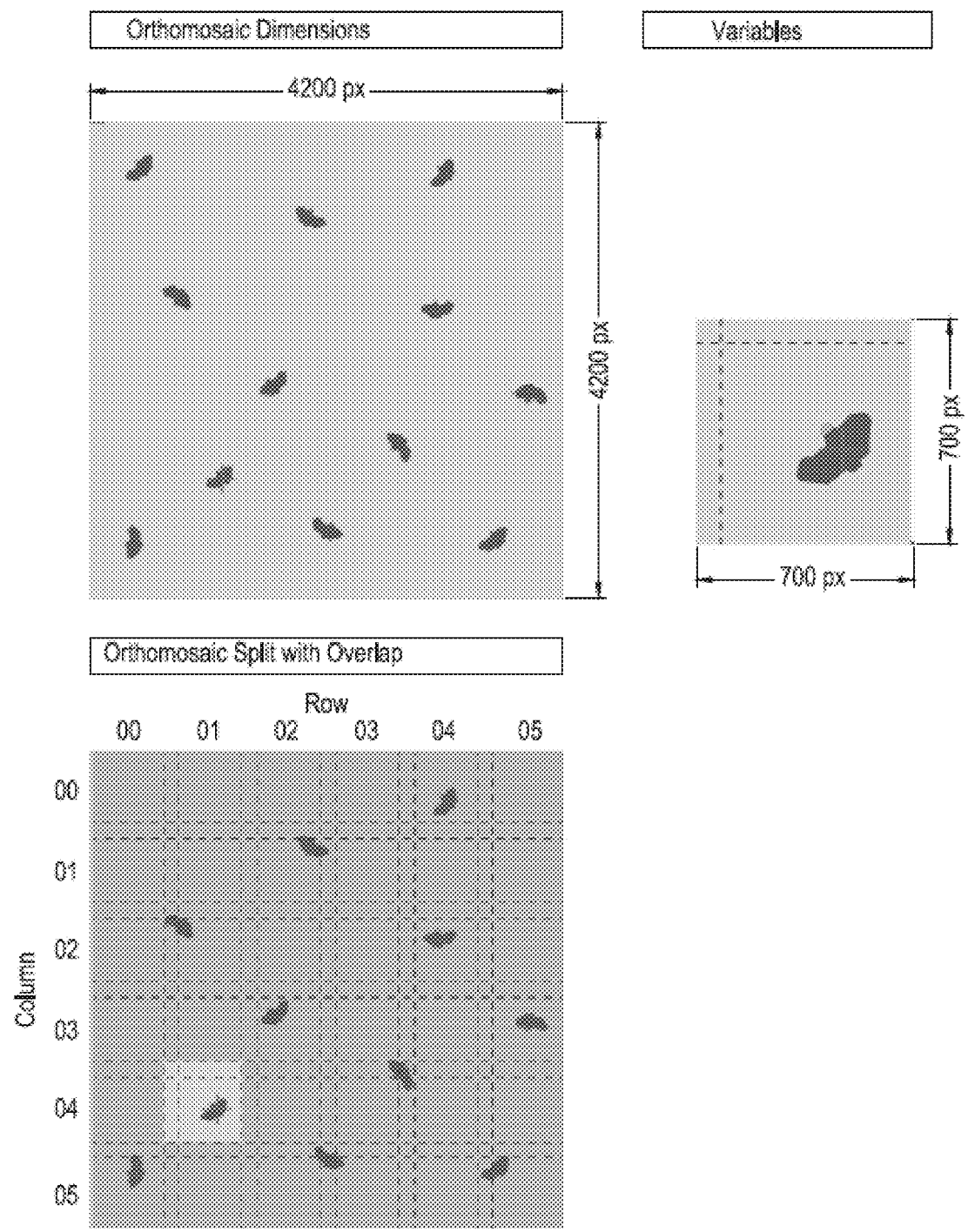

Referring to the right-hand image of FIG. 5, an example image of the area 32 with LUXO 33 is depicted as taken by the imaging device 34 of the UAV 31. The left-hand image of FIG. 5 is an example processed image as processed and labeled by the processing system 111. The lower image on FIG. 5 depicts a graphical representation of labeling an orthomosaic image used for training the processing system 111, using the trained processing system 111 to detect and identify LUXO in other images, and sample output data from the processing system 111 including predicted object coordinates and grade scores. Referring the three left-hand images of FIG. 6, the processing system 111 generates labeled orthomosaic image based on image data from the imaging device 34. The processing system 111 detects and labels the LUXO, and further generates split orthomosaic image of the labeled orthomosaic image. The split orthomosaic image(s) are used to train the machine learning model or the neural network. As such, referring to the right-hand images 4 FIG. 6 the processing system 111 has a trained machine learning model or the neural network and the processing system is capable of processing unlabeled orthomosaic image, splitting the unlabeled orthomosaic image to generate split unlabeled orthomosaic images with overlap, and using the trained machine learning model or the neural network to detect and identify LUXO in the split unlabeled orthomosaic images. The processing system can further output data of each identified LUXO and generate GIS shapefile(s). FIG. 7 depicts two example orthomosaic images with dimensions and one example orthomosaic image with overlapping orthomosaic images.

INCORPORATION BY REFERENCE

The entire contents of all patents, published patent applications and other references cited herein are hereby expressly incorporated herein in their entireties by reference.

EQUIVALENTS

In the present description, certain terms have been used for brevity, clarity, and understanding. No unnecessary limitations are to be inferred therefrom because such terms are used for descriptive purposes and are intended to be broadly construed. The different apparatuses, systems, and method steps described herein may be used alone or in combination with other apparatuses, systems, and methods. It is to be expected that various equivalents, alternatives and modifications are possible within the scope of the appended claims.

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments; as such, each member of the list should be considered a separate embodiment.

What is claimed is:

1. A system for detecting and identifying explosives in a target area using an unmanned aerial vehicle (UAV) comprising:

a UAV adapted to comprise an imaging device suitable to capture image data and a transmission component capable of transmitting said image data to a control system;

an explosives detection and identification processing module comprising the control system suitable to receive and process the image data transmitted from the UAV, and wherein the module comprises a machine-readable medium having instructions stored thereon for execution by a processor to perform a method comprising the steps of:

storing the image data received from the UAV on the machine-readable medium;

processing the image data to generate images of a training area with known explosives;

fusing the images of the training area to generate an orthomosaic image representative of the training area with the explosives;

analyzing one or more split images derived from the orthomosaic image using image processing algorithms, computer machine learning, computer vision machine learning (CVML), and/or an artificial neural network trained to detect patterns or predefined objects to generate a training model for automating the detection of explosives;

identifying and labelling the explosives in the training area in the orthomosaic image to refine the training model; and applying the refined training model to a target area to predict the location of unknown explosives in the target area by comparing trained orthomosaic image data from the target area to previously generated orthomosaic image data from training area, such that the system is suitable for detecting and identifying explosives in the target area using the unmanned aerial vehicle (UAV).

2. The system of claim 1 further comprises a GPS sensor component positioned on the UAV, suitable to capture positioning data and capable of transmitting said image data to the control system, wherein the control system is suitable to receive and process positioning data from the GPS sensor component and such data is fused into the orthomosaic image.

3. The system of claim 1, wherein the step of applying the refined training model to the target area comprises the steps of:

storing the target area image data on the machine-readable medium;

processing the target area image data to generate images of the target area with unknown explosives;

fusing the images of the target area to generate an orthomosaic image representative of the target area with the unknown explosives;

analyzing one or more split images derived from the orthomosaic image using the refined training model with image processing algorithms, computer machine learning, computer vision machine learning (CVML), and/or an artificial neural network (e.g., convolutional neural network (CNN)) to predict the location of unknown explosives in the target area by comparing trained orthomosaic image data from the target area to previously generated orthomosaic image data from training area; and identifying and labelling the explosives in the target area in the orthomosaic image.

4. The system of claim 3, wherein the data obtained in the identification and labelling of the explosives in the target area is used to further refine the training model to detect and identify unknown explosives.

5. The system of claim 1, wherein the imaging device is selected from the group consisting of a camera, visual-light sensor, multispectral sensor, a thermal sensor, and any combination thereof.

6. The system of claim 3, wherein the step of labelling the orthomosaic image includes marking with indicia selected from the group consisting of boxes, geometric systems, alphanumerical text, graphics, color, and any combination thereof.

7. The system of claim 1, wherein the method further comprises the step of producing an annotation file that contains a list of all labeled explosives and corresponding munition type and GPS location data.

8. The system of claim 1, wherein the location of the predicted explosives are displayed to the user via an output device selected from a web application.

9. An explosives detection and identification processing module comprising a control system suitable to receive and process the image data transmitted from an unmanned aerial vehicle (UAV), and wherein the module comprises a machine-readable medium having instructions stored thereon for execution by a processor to perform a method comprising the steps of:

storing the image data received from a UAV on the machine-readable medium;

processing the image data to generate images of a training area with known explosives;

fusing the images of the training area to generate an orthomosaic image representative of the training area with the explosives;

analyzing one or more split images derived from the orthomosaic image using image processing algorithms, computer machine learning, computer vision machine learning (CVML), and/or an artificial neural network trained to detect patterns or predefined objects to generate a training model for automating the detection of explosives;

identifying and labelling the explosives in the training area in the orthomosaic image to refine the training model; and applying the refined training model to a target area to predict the location of unknown explosives in the target area by comparing trained orthomosaic image data from the target area to previously generated orthomosaic image data from training area, such that the module is suitable for detecting and identifying explosives in the target area using the unmanned aerial vehicle (UAV).

10. The explosives detection and identification processing module of claim 9, wherein the control system is suitable to receive and process positioning data from a GPS sensor component and such data is fused into the orthomosaic image.

11. The explosives detection and identification processing module of claim 9, wherein the step of applying the refined training model to the target area comprises the steps of:

storing the target area image data on the machine-readable medium;

processing the target area image data to generate images of the target area with unknown explosives;

fusing the images of the target area to generate an orthomosaic image representative of the target area with the unknown explosives;

analyzing one or more split images derived from the orthomosaic image using the refined training model with image processing algorithms, computer machine learning, computer vision machine learning (CVML), and/or an artificial neural network to predict the location of unknown explosives in the target area by comparing trained orthomosaic image data from the target area to previously generated orthomosaic image data from training area; and identifying and labelling the explosives in the target area in the orthomosaic image.

12. The explosives detection and identification processing module of claim 11, wherein the data obtained in the identification and labelling of the explosives in the target area is used to further refine the training model to detect and identify unknown explosives.

13. The explosives detection and identification processing module of claim 11, wherein the step of labelling the orthomosaic image includes marking with indicia selected from the group consisting of boxes, geometric systems, alphanumerical text, graphics, color, and any combination thereof.

14. The explosives detection and identification processing module of claim 9, wherein the method further comprises the step of producing an annotation file that contains a list of all labeled explosives and corresponding munition type and GPS location data.

15. The explosives detection and identification processing module of claim 9, wherein the location of the predicted explosives are displayed to the user via an output device selected from a web application.

16. A method for detecting and identifying explosives in a target area using an unmanned aerial vehicle (UAV), the method comprising the steps of:

storing image data received from a UAV on a machine-readable medium;

processing the image data to generate images of a training area with known explosives;

fusing the images of the training area to generate an orthomosaic image representative of the training area with the explosives;

analyzing one or more split images derived from the orthomosaic image using image processing algorithms, computer machine learning, computer vision machine learning (CVML), and/or an artificial neural network trained to detect patterns or predefined objects to generate a training model for automating the detection of explosives;

identifying and labelling the explosives in the training area in the orthomosaic image to refine the training model; and applying the refined training model to a target area to predict the location of unknown explosives in the target area by comparing trained orthomosaic image data from the target area to previously generated orthomosaic image data from training area, such that the method is suitable for detecting and identifying explosives in the target area using the unmanned aerial vehicle (UAV).

17. The method for detecting and identifying explosives of claim 16, wherein the step of applying the refined training model to the target area comprises the steps of:

storing the target area image data on the machine-readable medium;

processing the target area image data to generate images of the target area with unknown explosives;

fusing the images of the target area to generate an orthomosaic image representative of the target area with the unknown explosives;

analyzing one or more split images derived from the orthomosaic image using the refined training model with image processing algorithms, computer machine learning, computer vision machine learning (CVML), and/or an artificial neural network (e.g., convolutional neural network (CNN)) to predict the location of unknown explosives in the target area by comparing trained orthomosaic image data from the target area to previously generated orthomosaic image data from training area; and identifying and labelling the explosives in the target area in the orthomosaic image.

18. The method for detecting and identifying explosives of claim 17, wherein the data obtained in the identification and labelling of the explosives in the target area is used to further refine the training model to detect and identify unknown explosives.

19. The method for detecting and identifying explosives of claim 17, wherein the step of labelling the orthomosaic image includes marking with indicia selected from the group consisting of boxes, geometric systems, alphanumerical text, graphics, color, and any combination thereof.

20. The method for detecting and identifying explosives of claim 17, wherein the method further comprises the step of producing an annotation file that contains a list of all labeled explosives and corresponding munition type and GPS location data.

21. The method for detecting and identifying explosives of claim 17, wherein the location of the predicted explosives are displayed to the user via an output device selected from a web application.

* * * * *